United States Patent [19]

Lopukhin et al.

[11] Patent Number: 5,587,295

[45] Date of Patent: Dec. 24, 1996

[54] METHOD FOR PRODUCING AFFINO-ENZYMATIC COMPOUNDS AND VISUALIZING AGENT AND APPLICATION THEREOF

[75] Inventors: Jury M. Lopukhin; Viktor V. Zvesky; Alexander B. Rabovsky, all of Moscow; Irina P. Andrianova, deceased, late of Moscow, all of Russian Federation, by Lev A. Andrianov, Dimitri B. Gudkov, executors, Ekaterina L. Andrianova, executrix

[73] Assignee: 2860601 Canada Inc., Toronto, Canada

[21] Appl. No.: 276,914

[22] Filed: Jul. 19, 1994

Related U.S. Application Data

[60] Division of Ser. No. 146,974, Dec. 9, 1993, Pat. No. 5,489,510, which is a continuation-in-part of Ser. No. 54,954, Apr. 28, 1993, abandoned, which is a continuation of Ser. No. 296,448, Jan. 11, 1989, abandoned.

[30] Foreign Application Priority Data

Jan. 19, 1988 [SU] U.S.S.R. ............................ 4357046

[51] Int. Cl.⁶ .......................... C12Q 1/60; G01N 31/00
[52] U.S. Cl. ............................. 435/11; 435/4; 435/7.1; 435/7.9; 435/20; 435/21; 435/22; 435/25; 435/28; 436/13; 436/63; 436/71; 436/501; 424/9.1
[58] Field of Search .................. 435/11, 4, 7.1, 435/7.9, 20, 21, 22, 25, 28; 436/13, 63, 71, 501; 424/9.1

[56] References Cited

PUBLICATIONS

Andrianova et al, Abstract from *Derwent* N89–195497, (Au 892578, Jul. 20, 1989 Australian Patent).

Lopukhin et al., *Chemical Abstracts*, vol. 115, Ref. #131406c, p. 517,1991 (Neth. Appl. NL 89 01,732, Feb. 1, 1991).

Lopukhin et al, *Chemical Abstracts*, vol. 113, p. 335, 1990 (Eur. Pat. Appl. EP 338,189, Oct. 25, 1989) Ref. #128987w.

Andrianova et al, *Chemical Abstracts*, vol. 105, pp. 313–314, Ref. #205747g, 1986 (Biol. Membr. 1986, 3(9) 931–5).

*Primary Examiner*—Michael G. Wityshyn
*Assistant Examiner*—Abdel A. Mohamed
*Attorney, Agent, or Firm*—Burgess, Ryan and Wayne

[57] ABSTRACT

The invention is a non-invasive diagnostic test which is performed on the surface of the skin. This test indicates skin cholesterol levels which can provide information about the extent of aortic atherosclerosis. The invention also relates to reagents in the form of affino-enzymatic test compounds for use in the diagnostic test.

8 Claims, 1 Drawing Sheet

METHOD FOR PRODUCING AFFINO-ENZYMATIC COMPOUNDS AND VISUALIZING AGENT AND APPLICATION THEREOF

RELATED CASES

This application is a division of U.S. patent application Ser. No. 08/146,974, filed Dec. 9, 1993, now U.S. Pat. No. 5,489,510 which is a continuation-in-part of U.S. patent application Ser. No. 08/054,954, filed Apr. 28, 1993, now abandoned, which is expressly incorporated herein by reference, which is a continuation of U.S. patent application Ser. No. 07/296,448, filed Jan. 11, 1989, now abandoned.

BACKGROUND OF THE INVENTION

1. Field of the Invention

The present invention relates to a method for the visual indication of cholesterol on the surface of skin utilizing affino-enzymatic compounds based on a cholesterol affinant binding agent and a visualizing agent, and methods for producing such compounds.

By virtue of its simplicity and non-invasive nature, the proposed invention is an ideal tool for mass examinations to identify individuals with advanced atherosclerosis as well as those at risk of developing this disease and other diseases which result in or are attributable to high blood cholesterol levels.

2. Description of Related Art

Many studies in recent years have shown that atherosclerosis and its complications such as heart attacks, strokes and gangrenes, are major causes of mortality in all countries of the world.

Cost effective prevention of atherosclerosis in a population require the identification of the high-risk group of individuals followed by their differentiated treatment and change of life style. The difficulty lies in deciding which individuals belong to the high-risk group.

Existing methods for diagnosing atherosclerosis are based on measuring general or total cholesterol content of venous blood plasma. (Consensus Conference on Lowering Blood Cholesterol to Prevent Heart Disease, JAMA, 1985, 253, pg. 2080; The Lipid Research Clinics Population Studies Data Book, publication 80–152, Bethesda, Ma, National Institute of Health, 1980, vol. I; Lipid Research Clinics Program, JAMA, 1984, 251, pg. 351–364). In some countries, a cholesterol content of over 240 mg/dL is considered sufficient to include a patient into the high-risk group. Unfortunately, total cholesterol levels do not accurately predict a patient's risk level.

A more precise diagnosis can be made by analyzing blood plasma lipoproteins and determining the atherogeneity index which is determined by dividing the difference between the total cholesterol and the high-density lipoprotein (HDL) cholesterol, by the high-density lipoprotein cholesterol:

$$\text{Atherogeneity Index} = \frac{\text{Ch (total)} - \text{Ch(HDL)}}{\text{Ch(HDL)}}$$

This index is considered superior for predicting the degree of atherosclerosis within the arteries. A patient is considered to belong to the high-risk group when his atherogeneity index is more than 3, and to the atherosclerosis group, when this index is over 5.6 (Klimov A.N. "Phenotyping of Lipoproteins", Methodological Recommendations of the USSR Ministry of Health, M., Medicine, 1975; Goldfourt v., Koltsman E., Neufeld H. N., total and High Density Lipoprotein Cholesterol in the Serum and Risk of Mortality. British Medical Journal, 1985, 290, pg. 1239–1243).

Use of these methods necessitates blood taking which is uncomfortable and poses a risk of infection. Detailed analysis of plasma lipoproteins and cholesterol is complicated and expensive. Moreover, recent studies showed that the blood plasma does not fully reflect the process of cholesterol accumulation which is typical for the arterial wall and other bradytrophic tissues. In one case out of three, quantification of total cholesterol and even a complete phenotyping do not correlate with the severity of atherosclerosis (See: Myasnikov A. L., "Hypertensive Disease", 1965, M., Medicine, pg. 300).

It has been shown that tissue cholesterol plays a leading role in development of atherosclerosis. Tissues referred to collectively as bradytrophic tissues, have been identified which accumulate cholesterol in the same way as the arterial wall. These studies have demonstrated a close correlation between cholesterol content in the arterial wall and the skin.

This correlation between cholesterol content in the arterial wall and skin was proved through direct measurement of cholesterol in skin samples. Specimens were frozen in liquid nitrogen and lyophilized; cholesterol was extracted with Folch reagent and quantified using traditional chemical or biochemical methods. (See: Nikitin Y. P., Gordienko I. A., Dolgov A. V., Filimonova T. A. "Cholesterol content in the skin and its correlation with lipid quotient in the serum in normals and in patients with ischemic cardiac disease", Cardiology, 1987, II, No. 10, P.48–51; Bouisson H., de Graeve, Solera M. L. et al. Ann. Biol. Clin., 1982, vol. 40, p.361–407). Unfortunately, this method is too complicated and painful to be useful for population screening.

U.S. Pat. No. 4,458,686 describes a method of quantifying the amount of glucose and ethanol localized in the blood directly under the skin or on its surface. This patent also discloses that it is possible to quantify the amount of cholesterol using cholesterol oxidase. The method is based on stoichiometric changes of oxygen concentration using redox enzymes, mostly oxidoreductases, specific to the substrate in question. According to this method, oxygen concentration changes are measured electrochemically; for instance, via polarography with the use of special equipment and a specially designed electrode. Such sophisticated instrumentation necessitates the services of highly skilled personnel for making diagnoses and inevitably and unfortunately limits the usefulness of this method for population screening.

PCT Application US 84/00888 proposes a detection-visualization complex where the binding and visualizing elements are linked directly or through a bridging agent. The complex is intended to detect low quantities of target molecules, including lipids in biological tissues. However, this method of detecting lipids can be used only in laboratory conditions and requires taking biological fluid or tissue samples from a patient. Again, the method is painful, multistaged and too complicated to be useful for population screening.

Correlation between cholesterol content in the skin and severity of atherosclerotic vascular lesions can be obtained through standard laboratory analysis of skin specimens. In addition to the pain involved in taking a skin sample, this method has other disadvantages because 1 mm thick skin specimens include various skin layers horny layer (average thickness 0.1 mm) and connective tissue (derma proper)

represented by two layers—papillary and retinal. Both layers have a good blood supply and, consequently, specimens include vessels and blood; they may also contain perspiratory and sebaceous glands and their secretions. The subcutaneous fat is located directly under the derma and may also get into specimens, i.e. heterogeneity of specimens may pervert the data on cholesterol accumulated in the skin. From this point of view, a method which can quantify the cholesterol content in the horny layer of the derma on the skin surface would be most accurate and preferred.

SUMMARY OF THE INVENTION

Advances in the understanding of the pathogenesis of atherosclerosis led to the concept of a "skin test" method to diagnose atherosclerosis. Any part of skin can be used for diagnostics but the most suitable is the surface of a palm because it does not have sebaceous glands whose secretions, like the horny layer of the skin, contain cholesterol which may affect diagnostic results. The purpose of the present invention is to provide a method for the visual indication of cholesterol in a patient's skin which does not require the taking of a skin sample, the reagents for use in such methods, and a method to synthesize the reagents.

The present invention achieves these goals by providing reagents in the form of affino-enzymatic compounds which are bifunctional in their nature. These compounds can selectively bind to the free cholesterol of the skin and subsequently be made visually detectable. At least two components are necessary to obtain such a compound; a binding agent A, selected from a group of substances capable of discriminately forming stable complexes with free cholesterol of the skin in order to give the whole bifunctional compound an affinity to cholesterol; and a visualizing agent B which permits detection of the bi-functional compounds bound to the skin cholesterol.

Through the use of a bridging agent C, the sensitivity and hence the usefulness of the resulting complex can be enhanced. Use of a bridging agent C can also broaden the range of useful compounds. Where a bridging agent C is not exmployed, the binding agent A must discriminately form stable complexes with both the visualizing agent B, and with the free skin cholesterol. Where a bridging agent C is employed, it can act as a bridging molecule between the binding agent A and the visualizing agent B to yield an A-C-B complex instead of the simple A-B complex.

In cases where the bridging agent C is a relatively large molecule, multiple binding agents A and multiple visualizing agents B can be attached to a single molecule of bridging agent C. Through modifying the synthesis procedure, this can allow greater amounts of binding agent A to be bound to the bridging agent C versus the amount of visualizing agent B present. Similarly, where the converse is desired, larger amounts of the visualizing agent B can be bound to the bridging agent C and lesser amounts of the binding agent A. The optimum balance of binding agent A and visualizing agent B will be selected in accordance of the relative activity of the specific agents selected to serve these rolls. Where for example the visualizing agent B is highly active enzyme, less of it will provide substantially equivalent results to a less active alternate.

In addition to allowing a range of A to B ratios in the final complex, the bridging agent C can help stabilize and protect the activity of the agents bound to it.

The reagents according to this invention greatly simplify the diagnosis of atherosclerosis. The test method itself is simple, painless, and does not require special instrumentation. A basic embodiment of the present invention can be used to determine to which of the three groups the examined patients belong: the atherosclerotic group, the risk group, or the healthy group.

DETAILED DISCUSSION OF THE INVENTION

The affino-enzymatic compounds for visual indication of cholesterol provided by the present invention, and the diagnostic method based on their use, are well suited for population screening. The method is so simple in operation that it does not require specialized personnel and can be used in domestic situations.

By way of example, an A-B, or an A-C-B complex prepared according to the present invention is placed on the skin of the palm. Following a 10 second to 10 minute incubation period, selected in accordance with the activity of the specific complex involved, the area is rinsed with clean water. During this initial incubation period, the A portion of the complex binds the entire complex to the cholesterol in the skin. The subsequent rinsing step stops the binding process and removes any of the complex which was not bound to the cholesterol present in the skin. An indicating agent D is then placed on the same area. The indicating agent D will then react with the visualizing agent B component of the remaining complex to cause a color change. After a second incubation period lasting from about 5 seconds to 15 minutes, the area is examined to determine if a color change is perceptible. Again, the duration of this second incubation period is selected in accordance with the activity of the specific agents being used. This color change will be dependent on, among other things, how much complex remained after the rinsing step. This is dependent on the amount of cholesterol present in the skin. By controlling the reaction times and the concentration of the agents involved, the color change may or may not be visually detectable depending on the amount of cholesterol in the skin.

In practice, one or more discrete drops of A-B or A-C-B complex are placed on the skin of the palm. Where more than one drop is employed, each drop may have an increased concentration of functional activity level of the complex.

After a short incubation period, all drops of the complex are rinsed off, and a drop of the indicating agent D is placed on each of the same areas. After a second incubation period, the appearance of each drop is examined. In subjects with a low cholesterol content in the skin, the color change will be visible only where the drop corresponding to the highest concentration/functional activity level of the complex was applied. In subjects with slightly higher skin cholesterol content, i.e., intermediate level, some of the drops corresponding to the lower initial concentrations/activities of the complex can still result in a visible color change. In subjects with a very high cholesterol content in the skin, the color change will be visible where even the lowest concentrations/functional activity levels of the complex were applied.

For example, where three initial drops of the complex are used, the concentrations/functional activity levels can be selected so that test subjects can be ranked into one of three categories based on the cholesterol content of the skin:

1. Normal or healthy
2. Higher than normal indicating higher risk of developing atherosclerosis.
3. Atherosclerotic Thus, in the predetermined incubation period, only one of the three drops will result in a visible color change in healthy individuals. This first drop acts as a control, and helps to demonstrate that the reagents are working properly. Two of the three drops will show a color change in individuals belonging to the risk group, and all three drops will show a color change with individuals belonging to the atherosclerotic group.

It is not intended to limit the scope of this invention to the method which was outlined above for illustrative purposes. One variation is to change the number of initial concentrations or functional activity levels of the initial complex, as well as the corresponding number of initial drops. Where three drops are used, test subjects can be differentiated into three or four groups depending on whether the highest concentration/activity level is selected to always result in a visible color change, thereby acting in part as a control, or whether it is used to discriminate between for example low, and very low skin cholesterol levels. Thus, two different drops can result in zero, one or two visible color change reactions, thereby providing a diagnosis which can have three possible outcomes. More drops of increasing initial concentration or activity level will result in more possible groups, such that any given number of initial concentrations/activity levels can be employed to result in a number of possible outcomes equal to or one greater than the number of initial concentrations/activity levels used.

Another possible variation is to use the same concentration/activity level for each initial drop of the A-B or AC-B complex, and to vary the concentration of the indicating agent D. In this case, the concentration of the indicating agent D becomes the rate limiting step in the color change reaction. The color change will be visible only when enough A-B or A-C-B complex remains after rinsing to react with the indicating agent D to result in a perceptible color change.

The above method could also be altered such that the B-component of the A-C-B or A-B complex acts as an inhibitor of a color change reaction. In this case, the indicating agent D would be comprised of two or more separate components which when mixed result in a color change reaction except when in the presence of adequate A-C-B or A-B complex where the B agent served the function of a visualization inhibitor. When used in this manner, the color change would be perceptible in all spots on subjects with low cholesterol levels, and no spots would show a perceptible color change on subjects with very high cholesterol levels.

As outlined above, the visualization agent B can act either to inhibit or bring about a color change reaction. It should also be pointed out that the color change may be from a state of color to no color, or from no color to color. In all cases, the key is that the total activity of the visualization agent B will be related to the amount of cholesterol in the skin. In this way, according to the present invention, the visualization agent B is employed to facilitate the detection of cholesterol in the skin.

Especially where an A-C-B complex is used, there is more than one way to vary the concentrations/functional activity levels of each initial drop. Different concentrations of the same complex could be used; or the same concentration of complexes with increasing functional activity levels (based on more or less of the A and B agents per each molecular of bridging agent C) could be used; or a combination or variation in the concentration and functional activity level could be used.

Also, the incubation periods can be varied to provide the differentiation necessary to a diagnosis. For example, using a number of spots of A-B or A-C-B complex of the same concentrations/functional activity level, the time allowed for the initial incubation could be varied. In persons with high skin cholesterol levels, even the spots corresponding to the shortest incubation period would result in enough of the complex being bound to the skin to result in a perceptible color change during the second incubation period during which the indicating agent D reacts with the bound A-B or A-C-B complex. Similarly, using a number of spots of A-B or A-C-B complex of the same concentrations/functional activity level and a fixed time for the first incubation period, the time during which the indicating agent D reacts with the bound A-B or A-C-B complex, the second incubation period, could be varied. Again, in persons with high skin cholesterol levels, even the spots corresponding to the shortest incubation period would result in a perceptible color change.

Finally, rather than relying on the human eye to detect the color change resulting from the reaction between the visualization agent and the indicating agent, a device could be employed for this purpose. Some form of electronic device for example, could be employed to quantitatively measure the color change and provide a numeric indication of the skin cholesterol level. This device could either measure the level of color developed after a predetermined incubation period, or it could measure the rate of color development over time. In either case only one drop of the A-B or A-C-B complex need be employed.

The kinetics of the various chemical reactions underlying this invention can be manipulated in several ways to provide the differentiation necessary to make a diagnosis. It should be noted that it is not intended to limit the scope of this invention to the basic variations which are outlined above. The concentrations of the various reagents employed, and the times allowed for the different reactions can both be varied to result in numerous effective variations of the present invention. Obviously two or more of the variations outlined above can be simultaneously employed to result in numerous other useful methods to result in a diagnosis according to the present invention.

According to the present invention, there are many compounds which can be usefully employed to fulfill the various functions representing: the binding agent A; the visualizing agent B; and the bridging agent C, which together form the A-B and A-C-B complex; and the indicating agent D.

The A-B or A-C-B complex must first selectively bind to free cholesterol of the skin, and then be made visually detectable. At least two components are necessary to obtain such a complex: a cholesterol binding agent A, selected from a group of substances able to discriminately form stable complexes with free cholesterol of the skin in order to give the whole bi-functional compound an affinity to cholesterol; and visualizing agent B which works in conjunction with an indication agent D to permit visual detection of the bi-functional A-B or A-C-B complex once it is bound to the cholesterol in the skin.

The binding agent A must be able both to form a stable complex either directly with a visualizing agent B or through a bridging agent C. Compounds which will discriminately bind with free cholesterol in the skin are useful under the present invention as cholesterol binding agents A. The following representative classes of compounds meet these criteria. However, the present invention is not to be limited to these compounds:

Steroid glycosides, containing as an aglycone a cyclopentaneperhydrophenanthrene fragment of the furostanole or spirostanole series, and an oligosaccharide fragment including 3 to 10 monosaccharide residues with linear or branched structures (Hinta P. H. "Structure and biological activity of steroid glycosides of spirostan and furostan series", Hishinev, Stinza, 1987, pg. 142); or Triterpene glycosides, containing an aglycone of alpha or beta-amyryl, lupane, hopane, dammarane, linostane or holostane series, and oligosaccharides comprising saccharide residues of branched or linear structure (Dekanosidze G. E., Chirva V. Y., Sergienko T. V., Uvarova N. I. "Study on Triterpene Glycosides", Tbilisi, Meznniereba, 1982; or Hydrophobic proteins, capable of discriminately forming a complex compound with cholesterol (Hlimov A. N., Titova G. V., Kozhevnikov H. A., Biochemistry, 1982, vol. 47, No. 2, pg. 226–232); Hlimov A. N., Hozhevnikov H. A., Klyueva N. N. et al. Voprosy Meal., Hhimii, 1984, vol. 30, NO. 3, p. 86–90; Titova G. V., Hlyueva N. N., Hozhevnikov H. A., et al. Biochemistry, 1980, vol. 45, No. 1, pg. 51–55); or Protein toxins, capable of discriminately forming complex compounds with cholesterol. They are obtained from bacteria, marine microorganisms, insects or snakes (Dalin M. V., Fish N. G. "Protein Toxins or Microorganisms", Moscow, Medicine, 1980); or Polyene antibiotics, capable of discriminately forming complex compounds with cholesterol (I. J. Katzenstein, A. M. Spielvogel, A. W. Norman, J. Antibiot., 27, 12, 1974, pg. 943–951; Jong ShangShyng, Wang Hsi-Hua, Clin. J. Microbiol., 1976, 9, (1–2), pg. 19–30; Readio Josephine D. et al. Biochim. Biophys. Acta, 1982, 685 (2), pg. 219–224); or High-affinity enzymes, whose substrate is cholesterol, and which have a high affinity to it. All of the above-mentioned publications are incorporated herein by reference.

Enzyme/substrate reactions resulting in a color change are particularly useful for the visualizing/indication function related to agent B and agent D. Various enzymes can be incorporated as agent B in the A-B or A-C-B complex, which can subsequently react with their substrates in the indication agent D in order to result in, or inhibit, a color change reaction.

While it is not intended to limit the present invention, to the following compounds, as a visualizing agent B, the following enzymes, are useful: acetylcholinesterase, tyrosinase, glucose-6- phosphate dehydrogenase, glucose oxidase, glucoamylase, β-D-galactosidase, peroxidase, alkaline or acid phosphatase, alphachymotrypsin or pyrophosphatase.

Under the present invention, an example of the A-B complex needed for the cholesterol skin test can be synthesized as follows:

The cholesterol affinant binding agent (A), selected from the group of steroid glycosides containing as an aglycone a cyclopentaneperhydrophenanthrene fragment of furostanole or spirostanole series, and oligosaccharide fragments including 3 to 10 monosaccharides residues with linear or branched structures, or from a group of triterpene glycosides in which the aglycone is from the alpha- or beta-amyryl, lupane, hopane, dammarane, linostane or holostane series, and which carry an oligosaccharide of 2 to 8 branched or linear residues, or from a group of hydrophobic proteins capable of discriminately forming complex compounds with cholesterol, or from a group of protein toxins capable of discriminately forming complex compounds with cholesterol which can be obtained from bacteria, marine microorganisms, insects or snakes, or from a group of polyene antibiotics capable of discriminately forming complex compounds with cholesterol, or from enzymes having a high affinity to cholesterol, which may first be chemically activated in solution, using a binding agent A/activator at the molar ratio 1:1–1:10, binding agent A of concentration 1 to 20 mg/ml, temperature 0° to 85° C., pH 4 to 11, for 0.25 to 48 hours.

To the solution obtained, a visualizing agent B is added, selected from among the following enzymes: acetylcholinesterase, tyrosinase, glucose-6-phosphate dehydrogenase, glucose oxidase, glucoamylase, β-D-galactosidase, peroxidase, alkaline or acid phosphatase, alpha-chymotrypsin or pyrophosphatase in A/B molar ratio=20:1 to 1:1. Then the solution is incubated at 0° to 25° C. for 0.25 to 48 hours, thereby producing the A-B complex.

Under the present invention, the binding agent A, the visualizing agent B or the bridging agent C may be pretreated in order to yield functional groups which are more highly reactive. This optional step, referred to herein as chemical activation, can increase the agent's affinity for the other compounds ultimately comprising the final affinoenzymatic complex, thereby facilitating the synthesis process. This extra step may also reduce the time needed for the subsequent synthesis steps to the minimum of the ranges cited. It should also be noted that where anhydride groups are utilized to attach the binding agent A, or the visualizing agent B to each other, or to the bridging agent C, care must be taken to ensure that the reactants are kept dry in order to preserve the utility of the anhydride groups.

Compounds able to transform functional groups of agents A, B or C or combination thereof into their reactable states are used as activators of these agents. Such groups as primary amine, carboxyl, alpha-glycol can be activated using the well-known azide, carbodiimide and succinamide methods, or the method of periodate oxidation. The most preferable are the periodate and carbodiimide methods which allow mild synthesis conditions and thereby preserve activity of immobilized enzymes.

As outlined above, the functional groups of visualizing agent B can also be subjected to chemical activation. In this case, agent B is activated in solution with B/activator molar ratio of 1:1–1:10, agent B concentration 1 to 20 mg/ml, at temperature 0° to 25° C., pH=4–11, for 0.25 to 48 hours. Then binding agent A, which is one of the above listed substances, is added to the solution to create an A/B molar ratio of 20:1–1:1, and the solution is incubated at 0° to 25° C. for 0.25 to 48 hours until the A-B complex is obtained.

In cases where the visualizing agent B is a high-molecular-weight compound such as an enzyme, and binding agent A is a low molecular-weight compound, for instance, a glycoside, a molecule of the A-B complex can contain only one molecule of visualizing agent B. However, the molar quantity of binding agent A, responsible for binding skin cholesterol in the A-B complex, can exceed the content of visualizing agent B by several times, according to the number of functional groups on the enzyme molecule capable of complexing with binding agent A without significant loss of enzymatic activity. In such compounds, the content of visualizing agent B, is limited when an enzyme is used due to the relatively large size of the enzyme molecule. The result is a relatively low sensitivity of the compounds thus obtained, and the need to increase incubation times in the diagnostic procedures.

In order to enhance the technical performance of affinoenzymatic compounds for visual indication of cholesterol on the skin, and in view of increasing their sensitivity, the above binding agent A and visualizing agent B can be joined indirectly using bridging agent C, taken from a series of relatively low-molecular weight asymmetric functional compounds, such as bromcyan, trichlortriazine or 2-amino-4,6-dichlor-3-triazine.

Under the present invention, the A-C-B complex needed for the cholesterol skin test can be synthesized as follows:

The desired A-C-B complex can be obtained in two ways: either binding agent A is first linked to bridging agent C and then visualizing agent B is added to the intermediate product (A-C) to obtain the A-C-B complex or the order of the steps can be changed such that the intermediate product is composed of B-C to which binding agent A is added.

In the first option, binding agent A is dissolved in a suitable solution, in concentration 1 to 20 mg/ml, then a low-molecular-weight asymmetric bi-functional bridging agent C, selected from the above-mentioned substances, is added to the solution to create an A/C molar ratio= 1:0.5–1:10. Suitable solutions include water, organic solvent, and aqueous solution of inorganic compounds. This solution is incubated at 0° to 120° C. for 0.25 to 48 hours; then visualizing agent B, selected from the above substances, is added to cream an A/B molar ratio of 20:1–1:1. This solution is incubated at 0° to 25° C. for another period of up to 48 hours to obtain the final production A-C-B complex.

To obtain an affino-enzymatic compound through the intermediate product C-B, visualizing agent B is dissolved in the usual manner in an aqueous-salt buffer with pH 4 to 11, in concentration 1 to 20 mg/ml. Then a low-molecular-weight asymmetric bi-functional bridging agent C, selected among the above substances, is added so that the B/C molar ratio is 1:0.5–1:10. The solution obtained is incubated at 0° to 25° C. for up to 48 hours; then binding agent A is added to give an A/B molar ratio=20:1–1:1, and the solution is incubated at 0° to 25° C. for 0.25 to 48 hours to obtain the A-C-B complex.

In fact, the best sensitivity of affino-enzymatic compounds for visual indication of cholesterol on the skin can be obtained through using as a bridging agent C, high-molecular-weight poly-functional compounds, such as polysaccharides, proteins or synthetic polymers, i.e., any high-molecular-weight compounds containing functional groups selected among the following: primary amines, carboxyl, hydroxyl, aldehyde, haloid anhydride, mixed anhydrides, iminoesters, azide, hydrazide, maleimide, isocyanate or epoxide.

Both the binding agent A, being one or a mixture of compounds listed above for this purpose, and visualizing agent B, also being one or a mixture of the compounds listed above for this purpose, can be independently immobilized by any one of these proposed bridging agents. The resulting A-C-B complexes allow wide variation in the A/B ratios contained. This is useful in controlling the activity levels of the binding and visualizing functions. For instance, when using a binding agent A with lower affinity to cholesterol, it is possible to significantly increase its molar content in the A-C-B complex.

Such affino-enzymatic compounds may be obtained as follows: binding agent A, which is one of the above substances or a mixture thereof, and visualizing agent B, which is also one of the above, are taken in an A/B molar ratio at 20:1–1:1 and dissolved in an aqueous salt solution with pH 4 to 11, and in concentration of each of the agents 0.1 to 20 mg/ml. A high-molecular-weight poly-functional bridging agent C, selected from polysaccharides, proteins or synthetic polymers according to the above, is added to the solution obtained to yield an A-BC molar ratio of 1:0.5–1:10. The solution is then incubated at 0° to 25° C. for 0.25 to 48 hours to obtain the A-C-B complex.

Among steroid glycosides used as binding agent A and containing as an aglycone a cyclopentaneperhydrophenanthrene fragment of furostanole and spirostanole series, and oligosaccharide fragment including 3 to 10 monosaccharide residues with linear or branched structures, the preferred are: agavosides A, B, C, D, F, H and G, trillin, funcoside C, D, E, F, G, or I, dioscin, gracillin, ptotodoscine, kikubasoponine, juncosides E and H, lanotigonine, desglycodigitonin, digitonin, tomatine, gitonin, rocosides C, D and E, polygonatin, tigogenin tetraoside, tigogenin hexaoside, kapsycoside, alliumosides B, C, D and E, desglycodesramnoparillin, desglycoparillin, parillin, sarmaparilloside, asparagosides C, D, G and H, juccoside B, protojuccoside H, lanotigoside, monoside, bioside, trioside, purpureagitoside, tomatine, alliogenin, liquotetraoside, karatavioside A, cyclosiversioside H. acanthophylloside C, alliofuroside A, alliospiroside A, cyclosiversioside F, tea saponin acanthophylloside B, tigonin (total), glycoside from *Calha polynatala* or cyclosiversioside G.

Among the above steroid glycosides more preferable are funcosides C1 D, E, F, G, or I, dioscin, rocosides, C, D, and E, lanotigonin, digitonin and tomatine. The most preferable are digitonin and tomatine.

Among triterpene glycosides used as binding agent A and containing an aglycone of alpha- or beta-amyril, lupane, hopane, dammarane, lanostane or holostane series, and oligosaccharide containing 2 to 10 saccharides residues with branched or linear structures, the most preferable are: escin, avenacin, tea saponin, alpha-gederine, kauloside C, stichinoside A, cyclamine, chinovine, saponins from sugar beets, hypsoside and triterpene glycosides obtained from *Fatsia japonlca*.

Among hydrophobic proteins used as binding agent A and capable of discriminately forming complex compounds with cholesterol, the most preferable are: Folch meilin protein, lysosomic proteins, proteins of mitochondria, fibrinogen, immunoglobulins, cerebrone, myoglobin, trypsin, cytochrome C, cytochrome P-450 or apo-proteins of lipoproteins.

Among protein toxins, used as binding agent A and capable of forming complex compounds with cholesterol, which are obtained from bacteria, marine microorganisms, insects or snakes, the most preferable are: streptolysins o, pneumolysins, listerio lysine, o-toxin C. 1 obtained from *Perfringens sp.* of A and C types, S-toxin C. 1. novvi of A and C types, Hemolysins C. 1 histolyticum, hemolysins C. 1 botulinum of C and D types, tetanolysine, cerebrolysins, alveolysine, turingeolysine or cytotoxin from *Metridium senile*.

Among polyene antibiotics useful as binding agent A and capable of forming complex compounds with cholesterol, the most preferable are amphotericin B, philipine or nystatin.

Among enzymes with a high affinity to cholesterol useful as the binding agent A, the most preferable are cholesterol oxidases, cholesterol dehydrogenases or cholesterol esterases.

Among all the above-listed cholesterol affinants useful as a binding agent A, namely: glycosides, hydrophobic proteins, protein toxins, polyene antibiotics and high-affinity enzymes, the most preferable are the glycosides. Due to their chemical stability, they are best able to withstand the synthesis conditions involving both organic solvents and high temperatures while retaining the ability to form complexes with skin cholesterol. The low molecular weight of the preferred glycosides makes it possible to obtain a compound with a high molar content of binding agent A, thus providing multiple points of interaction between the A-C-B complex and skin cholesterol.

The most preferable among glycosides are steroid glycosides which are more efficient in forming complexes with cholesterol compared to triterpene glycosides.

Hydrophobic proteins, protein toxins, polyene antibiotics and high-affinity enzymes can also be successfully employed in the practice of the present invention as the binding agent A. However, they introduce certain limitations in the method of producing affino-enzymatic compounds due to their relatively lower chemical stability and inactivation tendencies. Moreover, the high-molecular weight of these binding agents somewhat reduces sensitivity of the complexes and necessitates higher concentrations of the resulting complex and/or longer reaction/incubation times during the diagnostic procedure.

Preferably, enzymes which can serve as the visualizing agent B, which can be bound either directly, or via a bridging molecule C, with a binding agent A to produce affino-enzymatic compounds for the visual indication of cholesterol on the skin are selected from the following list: acetylcholinesterase, tyrosinase, glucose-6-phosphate dehydrogenase, glucose oxidase, glucoamylase, β-D-galactosidase, peroxidase, alkaline or acid phosphatase, alpha-chymotrypsin or pyrophosphatase; it is however, not the intention to limit this invention to these compounds.

Any of these enzymes can be used with any of the above-listed binding agents A; however, steroid glycosides are preferred.

The use of a bridging agent C enhances the technical performance of the method and facilitates the production of the resulting A-C-B complex while preserving the functional activity of agents A and B.

The most highly preferred A-C-B complexes under the present invention are complexes which use steroid glycosides which contain as an aglycone a cyclopentaneperhydrophenanthrene fragment from the furostanol or spirostanol series and oligosaccharide fragments including 2 to 10 monosaccharide residues with linear or branched structures as the cholesterol affinant binding agent A.

Such steroid glycosides possess high chemical stability and can be immobilized on a bridging polymer/agent C. Their stability enables synthesis of the A-C fragment under severe conditions when required; i.e. high temperatures and dissolution in organic solvents. The severe conditions can facilitate a high binding agent A content in the A-C-B complex. The A-C-B complexes for the visual indication of cholesterol on the skin may be obtained through the consecutive immobilization of binding agent A onto the bridging agent C under severe conditions followed by the immobilization of visualizing agent B onto the A-C fragment, in moderate conditions which help preserve the enzymatic activity of the visualizing agent B.

As bridging agent C, the following asymmetric low-molecular-weight bifunctional compounds can be used: bromcyan, trichlortriazine or 2-amino-4,6-dichlor-3-triazine.

As a preferable alternative, use of high-molecular-weight poly-functional compounds as the bridging agent C, allows a wide range of control over the proportions of agents A and B in the final complex. This makes it easier to synthesize the A-C-B complex with an optimal ratio between the number of points bridging the complex with the skin surface (binding agent A) and quantity of visualizing agent B.

To serve the role of a high-molecular-weight poly-functional bridging agent C, it is possible to use various polysaccharides, proteins or synthetic polymers, i.e., any high-molecular-weight compound containing any of the following functional groups: primary amine, carboxyl, hydroxyl, aldehyde, haloidanbydride, mixed anhydride, iminoester, azide, hydroxide, maleimide, isocyanate or epoxide. These bridging agents C can be coupled with any binding agent A and visualizing agent B to produce the A-C-B complex.

Copolymers of acrylic acid or maleic anhydride and N-vinylpyrrolidone are most preferred as the high-molecular-weight poly-functional bridging agent C. The most preferred of the copolymers is a copolymer of N-vinylpyrrolidone and maleic anhydride.

The synthesis reactions typically take place in suitable solvents. Aqueous salt buffers solutions which provide a buffering action within the pH range of 4 to 11, facilitate attaching agents A and B either to each other or to bridging agent C and also help prevent inactivation or inhibition of enzymes used in the present invention. Salts of borate, citrate, phosphate and other compounds are useful for this purpose. The salt concentration is selected to ensure a stable pH during immobilization but not so high as to cause denaturation of the enzyme. Obviously, where anhydride groups are utilized to bind the agents, aqueous solutions may be inappropriate.

Some of the binding agents A such as steroid glycosides, triterpene glycosides and polyene antibiotics, dissolve inadequately or incompletely in water and therefore require organic solvents. In these cases, polar aprotonic solvents can be used as, for instance; dimethylsulfoxide, N,N-dimethylformamide, hexamethanol, a 2:1 N,N-dimethylformamide/toluene mixture, or a 2:1 N,N-dimethylformamide/hexane mixture. In cases where the enzymes in the visualization agent B can be deactivated by these solvents, the A-C portion should first be synthesized then dried before being added to an aqueous salt buffer solution containing the detecting agent B to yield the final A-C-B complex.

Synthesis conditions required to produce the A-C-B or A-B complex for cholesterol indication (temperature, incubation time, etc.) depend on the choice of the A, B and C compounds. Use of enzymes as visualizing agent B limits the reaction temperature to 25° C. at most, and ideally, the reaction will typically be conducted at about 4° C. in buffer solution with pH at about 5 to 9. Use of synthetic polymers as bridging agent C, and glycosides for binding agent A allows the A-C reaction to take place in organic solvents at high temperatures (up to 120° C.). This allows a high yield of binding agent A to bind to the bridging agent C in a relatively short time.

Molar ratios of the components are selected in accordance with the molecular weights of the selected agents, their relative activity levels both with respect to each other, and ultimately with the skin cholesterol and the indication agent D employed.

It will be understood that unreacted components A, B and C if present can be removed from the complex A-B or A-C-B in a conventional manner such as by washing, by ion-exchange chromatography and the like. High purity concentrations of the complexes are not essential to perform the skin cholesterol test.

BRIEF DESCRIPTION OF THE DRAWINGS

The invention is illustrated by several examples and drawings.

Figure 1:
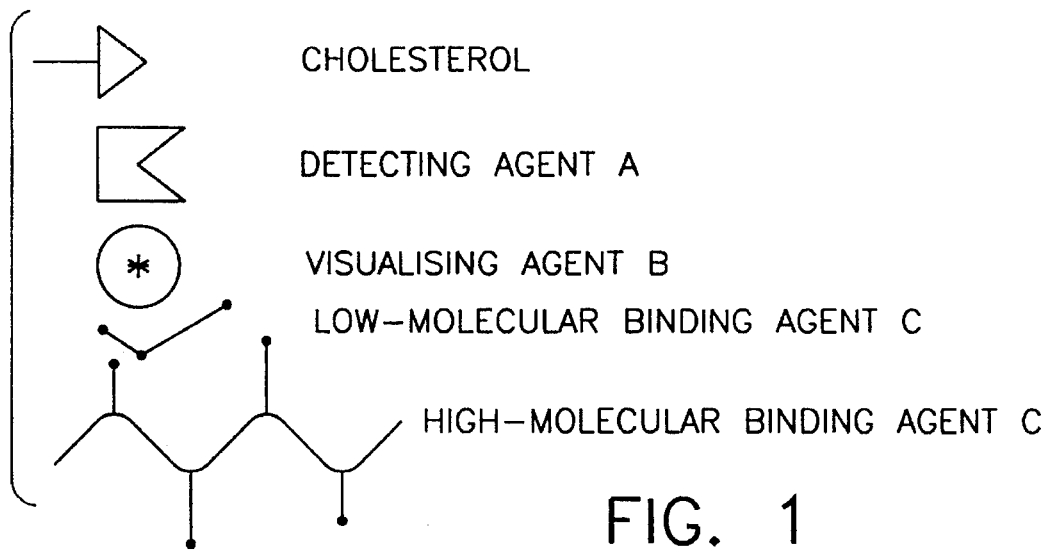
FIG. 1—presents an explanation of the symbols used in the other figures.
Figure 2:
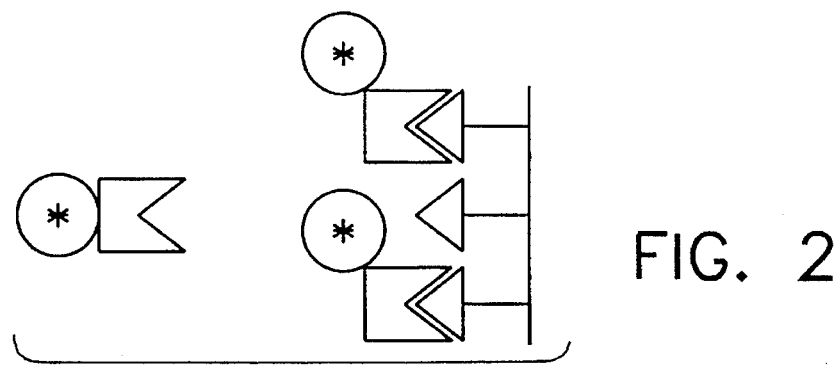
FIG. 2—Illustrates compounds obtained and their interaction with cholesterol on a patient's skin surface according to Examples 2, 3, 7 and 8.
Figure 3:
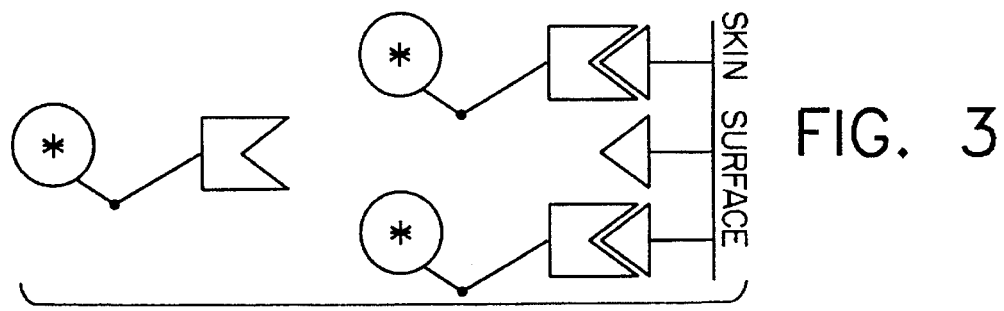
FIG. 3—Illustrates compounds obtained and their interaction with cholesterol on a patient's skin surface according to Example 5.
Figure 4:
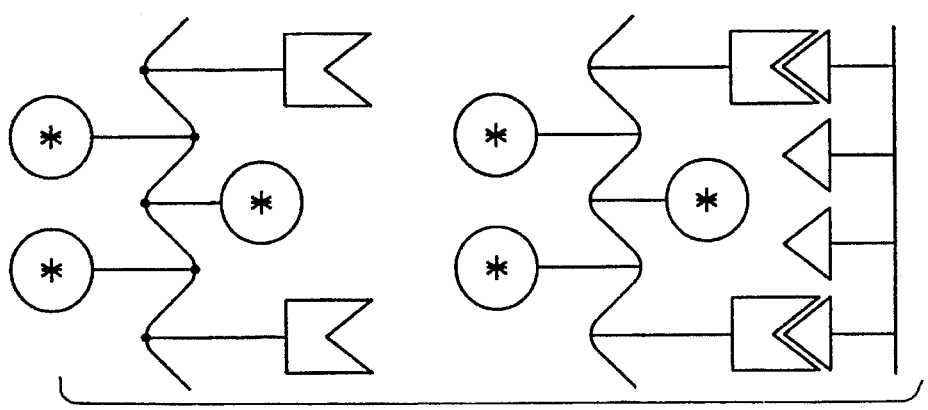
FIG. 4—Illustrates compounds obtained and their interaction with cholesterol on a patient's skin surface according to Examples 1, 4, 6, 9, 10, 11 and 12.

The following examples are included to further illustrate the invention.

EXAMPLE 1

Many commercial preparations of digitonin cannot be used directly because the preparations contain 30–50% material that cannot be dispersed evenly in water, and the effects of unpurified digitonin are unpredictable. The following method of purification is recommended. Dissolve 6 g of commercial digitonin (e.g., Serva or Sigma grade) in 150 ml absolute ethanol at 75° C. Digitonin is precipitated by chilling the solution at 0° C. (ice water) for 20 minutes and then separated by centrifugation at 4° C. This procedure is repeated twice, resulting in a 58% recovery (3.5 g) of originally used digitonin, obtained after vacuum drying in presence of phosphorus pentoxide.

In the first step the digitonin, the binding agent A, is bound to a copolymer of N-vinylpyrrolidone and maleic anhydride (with an average molecular weight of about 70,000 units) which serves as the bridging agent C. In this example, moisture must be thoroughly removed before the reaction. The reactants must also be activated. To this end, roughly, 0.5 g of the copolymer and 0.5 g of digitonin are placed (separately) in a drying chamber under a high vacuum and held for 4 to 5 hours at a temperature of 95°–100° C. over $P_2O_5$ (Note: Around 110° C. the copolymer will be degraded so careful temperature control is necessary.) The products are then allowed to cool to room temperature within the drying chamber.

In a small reaction chamber equipped with: stirring mechanism; heating jacket; thermometer; and reflux condenser, the cooled raw materials as prepared above are immediately dissolved in 5 ml of N,N-Dimethylformamide (DMF) upon their removal from the drying chamber.

The reactants are mixed and heated until all components are dissolved. After this point, the mixer may be switched off. The mixture is heated to 95° C. for 4 hours. The heater is switched off, and the mixture is allowed to cool to room temperature. Using a silicone oil bath this step typically takes 15–30 minutes. The mixer should now be turned on again. An additional 5 ml of N,N-Dimethylformamide is now added also at room temperature. After 5 minutes, 50 ml of acetone are added to cause a precipitate to form. After 30 more minutes, the contents of the reaction vessel are placed in a small lab centrifuge at 3000 rpm for about 10 minutes, or until clean separation is apparent. The liquids are then poured off, and another 15 acetone is thoroughly mixed in. Again the result is placed in a small lab centrifuge at 3000 rpm for about 10 minutes, or until clean separation is apparent. Three or more additional washing steps with 15 ml of acetone and centrifuging are used until the precipitate has the consistency of a solid powder.

The final product is dried in a in vacuum at 40° C. for 24 hours. The above quantities should yield about 0.7 to 0.9 g of product which has a light beige/brown color.

The amount of bound digitonin may now be measured. Ideally 350 to 400 mg of digitonin should be in each gram of copolymer digitonin conjugate (e.g., 37% digitonin: 63% copolymer by weight). Digitonin content may be measured using the method according to Dubois M. et al; Analytical Chemistry 1956, 23, 350–356; which measures total sugars.

Again, prior to the reaction coupling the peroxidase, visualization agent B, to the intermediate A-C complex synthesized as indicated above, the reagents should be thoroughly dried and activated.

The co-polymer-digitonin complex (A-C) is placed in a drying chamber under a high vacuum and held for 4 to 5 hours at a temperature of 95°–100° C. over $P_2O_5$. At temperatures nearing 110° C. the copolymer can be degraded so careful temperature control is necessary. This product is then allowed to cool to room temperature within the drying chamber.

In a very small reaction chamber (bottle) in a 0°–4° C. ice bath equipped with a magnetic stirrer; 5 mg horse-radish peroxidase is dissolved in 1 ml of 0.1M phosphate buffer with a pH of 7.5 after this is completely dissolved, a total of 10 mg of the digitonin-co-polymer complex is added. This reaction occurs at 4° C. while the mixing continues. Typically this reaction is allowed to procede overnight; however, it is likely substantially complete within minutes. Alkaline peroxidase is preferred because acid peroxidase tends to lose its activity when it is bound to the complex.

The reaction mixture containing the final product is then poured onto a column with a DEAE carrier. (Note: DEAE-Sepharose CL-6B is good, as is Cellulose, maybe the best medium is DEAE-TOYOPEARL from Tosh Corporation in Japan.) The total volume of the column used is just 1–3 ml. Before the separation, the column is washed with 0.1N phosphate or phosphate citrate buffer with pH 6.0. Next the reaction mixture is added to the column, and the first fraction is collected. This first fraction will contain the free digitonin and free peroxidase. The volume of this first fraction will be about 3 ml per each ml of column volume.

Next, another buffer 0.1N phosphate or phosphate citrate buffer with pH 6.0 plus 0.5M NaCl is added to the column. Again 2 or 3 ml per ml of column volume are passed through the column. This second fraction contains the final product.

The enzyme activity of the second fraction should be 10 to 15 percent of the total activity of the activity of the first fraction plus the activity of the second fraction. (Enzyme activity can be measured by Worthington or other standard method.)

The product is then desalanated by gel filtration using Sephadex G-25. Finally, 20–30 mg/ml lactose is added to increase stability, and the final A-C-B complex is freeze dried.

EXAMPLE 2

In the first step, 100 mg of tomatine (A) are mixed well in 10 ml of water. 40 mg of sodium periodate are added, and the mixture is incubated in the dark at 20° C. for 4 hours. To the resultant solution, 1 ml of alpha-chymotrysin solution (B) (10 mg/ml) in 0.2M phosphate buffer with pH=7.5 is added and the mixture is incubated for 12 hours at 4° C. The result is a solution of the final A-B complex.

EXAMPLE 3

In the first step, 3 mg of horseradish peroxidase (B) is dissolved in 1 ml of water, 0.5 mg of sodium periodate is added, and the mixture is incubated for 8 hours at 4° C. Next, 3 mg of cholesterol oxidase (A) in 1 ml of 0.2M phosphate buffer with pH −7.5 is added to the solution obtained in the first step, and the mixture is incubated for another 12 hours at 4° C. The result is a solution of the final A-B complex.

EXAMPLE 4

In the first step, 10 mg of polyacrylic acid (C) is dissolved in 10 ml of acetate buffer with pH 4.8, and 15 mg of p-cyclohexyl-2-(4-mofoline)ethyl-carbodiimide-meta-p-toluene sulfonate are added. The mixture is then incubated for 1.5 hours at 0° C. Next, 5 ml of buffer containing 5 mg of streptolysins o (A) and 5 mg of horseradish peroxidase (B) are added to the thus obtained solution. The mixture is incubated for 2 hours at 20° C. The result is a solution of the final A-C-B complex.

EXAMPLE 5

In the first step, 100 mg of agavoside G (A) are placed in 5 ml of water, and 100 mg of bromycyan (C) are added; a pH of about 11 is maintained by adding 1M NaOH solution. The mixture is then incubated for 30 minutes at 4° C. and the pH is reduced to 8.5 by adding phosphoric acid. Next, 3 ml of 0.5M phosphate buffer with pH 8.5 containing 6 mg of alkaline phosphatase (B) are added to 1 ml of the thus obtained solution. This mixture is then incubated for 12 hours at 4° C. The result is a solution of the final A-C-B complex.

EXAMPLE 6

In the first step, 500 mg of nystatin (A) and 250 mg of a copolymer of ethylene with maleic anhydride (C) are dissolved in 5 ml of N,N-dimethylformamide and incubated in an argon current at 50° C. for 3 hours. The product obtained is precipitated in 20 ml of ethyl acetate, and dried in vacuum at 20° C. Next, 6 mg of the product obtained are added to 1 ml of $\beta$-D-galactosidase (B) solution (2 mg/ml) in 0.2M phosphate buffer with pH=7.5, and this mixture is then incubated at 4° C. for 12 hours. The result is a solution of the final A-C-B complex.

EXAMPLE 7

In the first step, 80 mg of digitonin (A) is dissolved in 10 ml of water, 30 mg of sodium periodate is added and the mixture is incubated in the dark for 6 hours at 20° C. Next, 1 ml of peroxidase (B) with the content of peroxidase 6 mg/ml in 1M phosphate buffer and pH 7.0 is added to the solution obtained, and the mixture is incubated for 24 hours at 4° C. The result is a solution of the final A-B complex.

EXAMPLE 8

In the first step, 70 mg of escin (A) is dissolved in 10 ml of water, 20 mg of sodium periodate is added and the mixture is incubated in the dark for 24 hours at 4° C. To 1 ml of the resultant solution, 1 ml of peroxidase solution (B) with peroxidase content of 4 mg/ml in 0.05M phosphate buffer and pH 7.0 is added. The mixture is incubated for 12 hours at 4° C. The result is a solution of the final A-B complex.

EXAMPLE 9

In the first step, 1 mg of peroxidase (B) and 6 mg of nystatin (A) are dissolved in 2 ml of 0.2M phosphate buffer with pH 7.0, and 8 mg of polyacrylic acid chloranhydride (C) is added to the solution. The mixture is then incubated for 24 hours at 4° C. The result is a solution of the final A-C-B complex.

EXAMPLE 10

In the first step, 100 mg of phylipine (A) and 150 mg of maleic anhydride copolymer with styrol (C), are dissolved in 2 ml of dimethylformamide. Next, the resultant mixture is heated in an argon stream to 90° C. for 2 hours. The reaction mixture is cooled, 2 ml of N,N-dimethylformamide is added, and the product is precipitated with 5 ml of acetone. The resultant residue is dried under vacuum over phosphorus pentoxide for 8 hours at 70°–80° C. To 1 ml of alkaline phosphatase solution (B) containing 2 mg/ml of alkaline phosphatase in 0.1M phosphate buffer, pH 7.5, 4 mg of the dried product obtained above is added, and the mixture is incubated for 18 hours at 4° C. The result is a solution of the final A-C-B complex.

EXAMPLE 11

In the first step, 80 mg of digitonin (A) and 100 mg of maleic anhydride copolymer with N-vinylpyrrolidone (C) are dissolved in 1 ml of N,N-dimethylformamide, and the mixture is incubated for 4 hours at 90° C. The mixture is cooled, 1 mg of N,N-dimethylformamide is added, and the product is precipitated with 4 ml of acetone. The residue is dried under vacuum over phosphorus pentoxide at 100° C. for 4 hours. To 1 ml of the solution containing peroxidase (B), 3 mg/ml in 0.1M phosphate buffer pH 7.5, 5 mg of the resultant product (A-C) is added, and the mixture is incubated for 12 hours at 4° C. The result is a solution of the final A-C-B complex.

EXAMPLE 12

In the first step, 50 mg of escin (A) and 100 mg of the copolymer of N-vinylpyrrolidone with maleic anhydride (C) are dissolved in 1 ml of dimethylsulfoxide and incubated for 2 hours at 100° C. The product obtained is precipitated using 3 ml of acetone then dried under a vacuum in the presence of phosphorus pentoxide for 4 hours at 100° C. Next, 8 mg of the product obtained are added to 1 ml of alpha-chymotrysin solution (B) (1 mg/ml) in 0.2M phosphate buffer with pH=7.5, and the mixture is incubated at 6° C. for 15 hours. The result is a solution of the final A-C-B complex.

In this final example, like the first example which represents the preferred embodiment, the high-molecular-weight of bridging agent C, coupled with the high reaction temperatures yields a high molar content of binding agent A in the intermediate A-C fragment. The visualizing agent B is then added under mild conditions to preserve its enzymatic activity.

Use of the compounds for visual indication of cholesterol on the patient's skin.

Diagnosis using the complexes produced according to the present invention allow patients to be grouped into categories based on their degree of atherosclerotic risk.

A few square centimeters of skin area selected on any part of the body, are sufficient for a diagnostic procedure; however, the most preferable is the palm of the hand, which is easily accessible and has no sebaceous glands.

In the first step of the preferred embodiment of the diagnostic procedure, single drops of the complex obtained are applied in different concentrations/activity levels on the surface of the skin of the palm, and incubated for an initial period lasting from about 15 seconds to 15 minutes.

The concentrations/activity levels are selected in accordance with the number of different drops employed and the time allowed for the reaction. By way of example, using the A-C-B complex-prepared according to Example 1, the final complex will typically constitute by weight roughly 30:60:10 of the agents A:C:B; in this case Digitonin:Copolymer:Peroxidase. Upon synthesis, the specific peroxidase activity of the complex will typically be 2 units/mg, as estimated according to the method set out in the Worthington Manual, pg. 67. (Method using 4-amino-anitpyrine) To use this compound for a three drop test such that the color change is perceptible even in healthy individuals (the first drop acts as a control to show the reagents are working); the preparation is diluted to give activities of approximately 0.75, 0.15, and 0.05 units. Single drops of the A-C-B complex with these activities are placed on the palm.

After an incubation period of one minute, the excess A-C-B complex, not bound to skin cholesterol, is removed by rinsing with de-ionized distilled water. Then, a single drop of an indicator agent D is applied to each of the areas on the skin.

The indicator agent D typically contains a substrate of the enzyme employed as the visualizing agent B, and additional compounds needed to make the reaction between the enzyme and its substrate visible. In this example, based on a peroxidase enzyme, the indicator agent D may contain, 0.004 mg hydrogen peroxide, 4 mg of N,N-diethyl-p-phenylenediamine sulfate (which produces a pink to red color upon oxidation), 0.9 mg of $Na_2S_2O_3$ (a stabilizing solution), and 10 mg of KCl (which prevents excessive oxidation of the substrate), dissolved in 1 ml of a 0.1M phosphate buffer with a pH of 6.5. This formulation will remain colorless for 6 to 8 hours in the absence of the peroxidase and retain its color developing properties in concentrations up to about 4 mg/ml of the N,N-diethyl-p-phenylenediamine sulfate.

The hydrogen peroxide in the presence of the peroxidase is broken down into water and oxygen. The oxygen produced reacts with the N,N-diethyl-p-phenylenediamine sulfate to cause a color change. Within, for example, a 30 second time allowed for this reaction, the maximum concentration drop of the A-C-B complex should lead to the development of a perceptible red/pink color in all subjects, including normals in whom the skin cholesterol content is the least. This first colored spot acts as a control to verify that the reagents are working properly.

Within the 30 seconds, the spot corresponding to the minimum concentration of the A-C-B complex should yield a perceptible color change only in patients having the clinical form of atherosclerotic disease in whom the cholesterol content is the greatest. The A-C-B complex solution with intermediate concentration should yield a perceptible color change both in atherosclerotic patients and in subjects belonging to the risk group (high cholesterol content), but not in healthy individuals. Obviously, the time allowed for the color change reaction is selected in accordance with the concentrations of the various reagents employed. It is not the intention to limit the scope of the present application to the 30 seconds used herein by way of example.

Thus, in this example embodiment, three different concentrations of compounds produced according to this preferred embodiment of this invention are applied on a patient's skin. With one perceptible color change, a patient is considered to belong to normals, with two, to the risk group, and in case of three perceptible color changes, to clinical stage atherosclerotic patients.

Generally speaking, the indicator agent D is selected in accordance with the visualizing agent B. Many different substrates can be usefully employed in this function. By way of example, any of the following solutions can be usefully employed as a substrate of the peroxidase enzyme:

Solution 1: Peroxide (Hydroperitis; $H_2O_2$- urea complex) and 4 mg of N,N-diethyl-p-phenylenediamine sulfate, 0.9 mg of $Na_2S_2O_3$, and 10 mg of KCl, dissolved in 1 ml of a 0.1M phosphate buffer with a pH of 6.5. The final concentration of $H_2O_2$ will typically be 0.03%.

Solution 2: ABTS [2,2'-azino-bis-(3-ethylbenzthiazoline-6-sulfonic acid)]1 mM. hydrogen peroxide-0,002% in phosphate-citrate buffer with pH=4.3;

Solution 3: 3,3', 5.5'-tetramethylenebenzidine 0.4 mM, hydrogen peroxide 0.004% in acetate buffer with pH=6;

Solution 4: o-phenylenediamine 4 mM, hydrogen peroxide 0.004% in phosphate-citrate buffer with pH=5; or other peroxidase substrates widely used in immuno-enzymatic analysis.

Or if alkaline phosphatase is used as visualizing agent B, the following solution can be used as a substrate of this enzyme: p-nitrophenol phosphate 2.5 mM, magnesium chloride 0.5 mM in diethylamine buffer with pH=9.5; or any other alkaline phosphatase substrate used in immuno-enzymatic analysis.

U.S. Pat. No. 2,981,606 provides a detailed description of such color indication compositions and is incorporated herein by reference.

Results of preliminary testing of 200 patients with verified diagnosis are shown in Table 1. These results are based on tests according to the procedure taught herein using an A-C-B complex synthesized according to Example 1. These results show a high correlation between the proposed diagnostic method and the level of atherosclerotic vascular lesions.

TABLE 1

|  | Family hyprlipidemia | Ischemic heart disease | Hypertension | Ischemic heart disease + hypertension | Ischemia of lower extremities | Ischemic heart disease + hypertension + ischemia of lower extremities | Normals |
| --- | --- | --- | --- | --- | --- | --- | --- |
| No. of patients | 9 | 7 | 44 | 30 | 8 | 66 | 30 |
| Females (F) | 5 | 2 | 13 | 12 | — | — | 15 |
| Males (M) | 4 | 5 | 31 | 18 | 8 | 66 | 15 |
| Age (middle) | F-45, M-40 | F-55, M-47 | F-50, M-52 | F-54, M-52 | 48 | 54 | F-24, M-26 |
| Plasm cholesterol | 421.4 ± 135.6 | 252.0 ± 54.6 | 238.4 ± 51.4 | 290.5 ± 78.6 | 218.6 ± 51.5 | 239.6 ± 41.3 | 188.0 ± 34.0 |
| Atherogeneity Index | 10.0 ± 3.3 | 5.4 ± 1.9 | 5.4 ± 1.7 | 7.6 ± 2.9 | 5.1 ± 1.8 | 5.7 ± 2.6 | 3.6 ± 1.3 |
| Skin assay according to invention | 3 stains in all | 3-stains-3 2 stains-4 | 3 stains-10 2 stains-3 | 3 stains-24 2 stains-6 | 3 stains-6 2 stains-2 | 3 stains in all | 1 stain in all |

What is claimed:

1. An affino-enzymatic agent which comprises a binding agent A which binds with cholesterol in the surface of the skin and a visualizing agent B which is bound to the binding agent A to permit color detection of the affino-enzymatic agent.

2. The affino-enzymatic agent of claim 1 wherein the visualizing agent B comprises at least one member selected from the group consisting of acetylcholinesterase, tyrosinase, glucose-6-phosphatedehydrogenase, glucose oxidase, glucose amylase, β-D-galactosidase, peroxidase, alkaline or acid phosphatase, alpha-chymotrypsin and pyrophosphatase.

3. The affino-enzymatic agent of claim 1 wherein the binding agent A comprises at least one member selected from the group consisting of steroid glycosides, triterpene glycosides, hydrophobic proteins which selectively form complexes with cholesterol, protein toxins which selectively form complexes with cholesterol, polyene antibiotics which selectively form complexes with cholesterol and enzymes having a high affinity for cholesterol and wherein the visualizing agent B comprises at least one number selected from the group consisting of acetylcholinesterase, tyrosinase, glucose-6-phosphatedehydrogenase, glucooxidase, glucoamylase, β-D-galactosidase, peroxidase, alkaline or acid phosphatase, alpha-chymotrypsin and pyrophosphatase.

4. The affino-enzymatic agent of claim 3 wherein the binding agent A is bound to the visualizing agent B by a bridging agent C to form a compound of the structure A-C-B.

5. The compound of claim 4 wherein the bridging agent C comprises at least one member selected from the group consisting of N-vinylpyrrolidone-maleic anhydride copolymer, polyacrylic acid, ethylene-maleic anhydride copolymer, polyacrylic acid, chloranhydride copolymer, and styrol-maleic anhydride copolymer.

6. The affino-enzymatic agent of claim 4 wherein the visualizing agent B comprises at least one member selected from the group consisting of acetylcholinesterase, tyrosinase, glucose-6-phosphatedehydrogenase, glucose oxidase, glucosoamylase, β-D-galactosidase, peroxidase, alkaline or acid phosphatase, alpha-chymotrypsin and pyrophosphatase.

7. The affino-enzymatic agent of claim 4 wherein the bridging agent C is a poly-functional compound containing at least two functional groups selected from the group consisting of primary amino, carboxyl, hydroxyl, aldehyde, haloid anhydride, mixed anhydride, iminoester, azide, hydrazide, maleimide, isocyanate and epoxide.

8. The affino-enzymatic compound of claim 7 wherein the poly-functional compound is a copolymer of acrylic acid or maleic anhydride and N-vinylpyrrolidone.

* * * * *